(12) United States Patent
Springett et al.

(10) Patent No.: US 9,622,993 B2
(45) Date of Patent: Apr. 18, 2017

(54) THIOSEMICARBAZONES INHIBITORS OF LYSOPHOSPHATIDIC ACID ACYLTRANSFERASE AND USES THEREOF

(71) Applicant: H. LEE MOFFITT CANCER CENTER AND RESEARCH INSTITUTE, INC., Tampa, FL (US)

(72) Inventors: Gregory Springett, Tampa, FL (US); Said M. Sebti, Tampa, FL (US); Nicholas J. Lawrence, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 15/302,640

(22) PCT Filed: Apr. 7, 2015

(86) PCT No.: PCT/US2015/024657
§ 371 (c)(1),
(2) Date: Oct. 7, 2016

(87) PCT Pub. No.: WO2015/157242
PCT Pub. Date: Oct. 15, 2015

(65) Prior Publication Data
US 2017/0027893 A1    Feb. 2, 2017

(51) Int. Cl.
C07D 305/08    (2006.01)
A61K 31/175    (2006.01)
A61K 31/4412    (2006.01)
C07C 337/08    (2006.01)

(52) U.S. Cl.
CPC ........ *A61K 31/175* (2013.01); *A61K 31/4412* (2013.01); *C07C 337/08* (2013.01)

(58) Field of Classification Search
None
See application file for complete search history.

(56) References Cited

U.S. PATENT DOCUMENTS

2003/0187007 A1* 10/2003 Cao ........................ C07C 281/14
                                                                        514/277

* cited by examiner

*Primary Examiner* — Karl J Puttlitz
(74) *Attorney, Agent, or Firm* — Meunier Carlin & Curfman LLC

(57) ABSTRACT

Lysophosphatidic acid acyltransferase-beta (LPAAT-β) catalyzes the production of phosphatidic acid (PA) from lysophosphatidic acid (LPA). The lipid cofactor PA contributes to the activation of c-Raf, BRAF, mTOR and PKC-ζ. LPAAT-β expression is a prognostic factor in gynecologic malignancies and is being investigated as a therapeutic target in a variety of tumor types. A class of thiosemicarbazones was identified as inhibitors of LPAAT-β from a screen of a library of small molecules. A focused library of thiosemicarbazones derivatives was prepared and led to the development of compounds which potently inhibit LPAAT-β and inhibit the growth of MiaPaCa2 human pancreatic cancer cells.

15 Claims, 16 Drawing Sheets

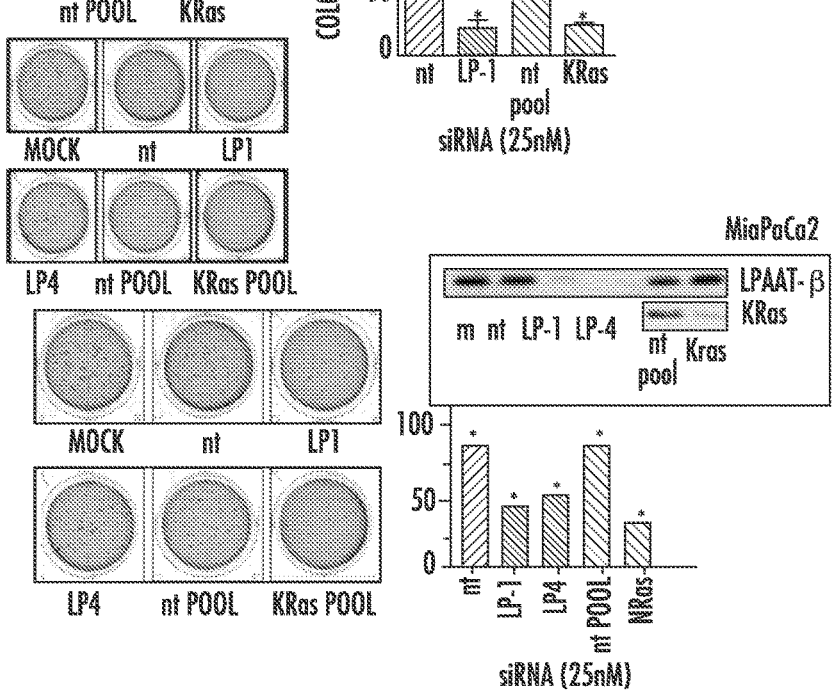

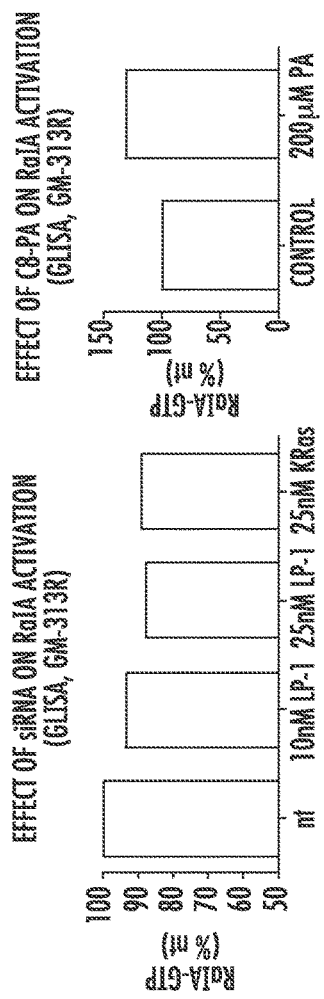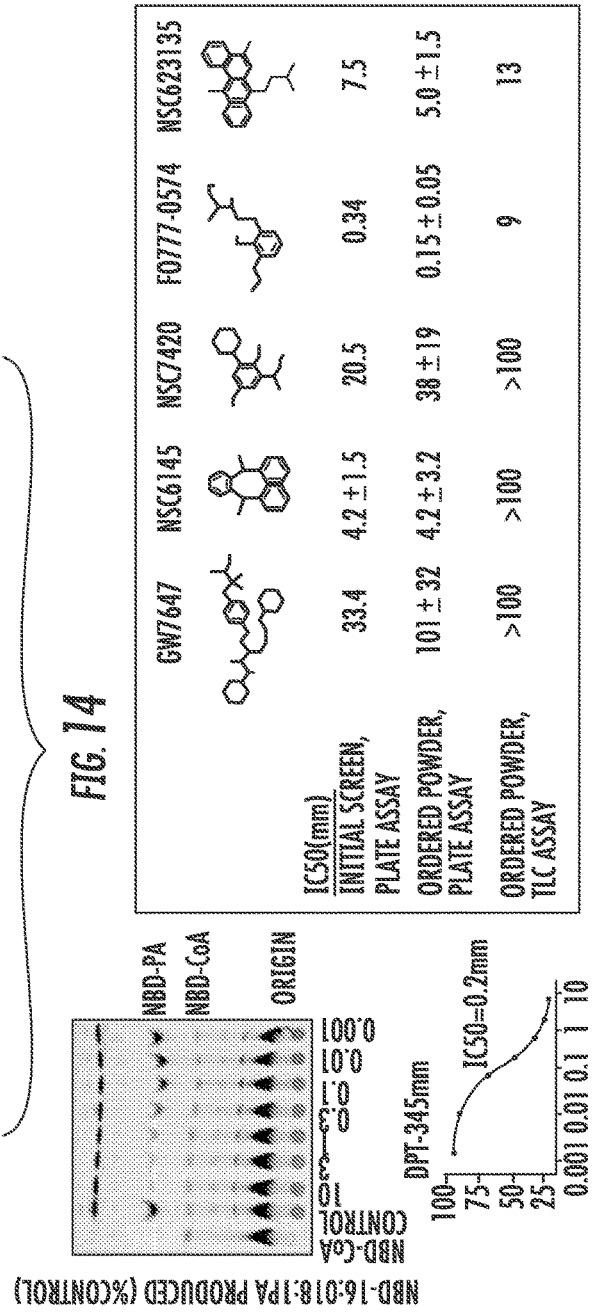
FIG. 14
FIG. 15

THIOSEMICARBAZONES INHIBITORS OF LYSOPHOSPHATIDIC ACID ACYLTRANSFERASE AND USES THEREOF

ACKNOWLEDGEMENT OF GOVERNMENT SUPPORT

This invention was made with Government support under Grant No. CA131400 awarded by the National Institutes of Health. The government has certain rights in this invention.

BACKGROUND

Phosphatidic acid (PA) is a cofactor required for the full activation of several signaling pathways prominent in cancer cells; among these are Raf family members, PKC-ζ, SOS and mTOR. (Bonham et al., Lysophosphatidic acid acyltransferase-beta: a novel target for induction of tumour cell apoptosis. *Expert Opin. Ther. Targets* 2003, 7, 643-61; Zhao et al., Phospholipase D2-generated phosphatidic acid couples EGFR stimulation to Ras activation by Sos. *Nat. Cell Biol.* 2007, 9, 706-12; Zhang et al., Phosphatidic acid signaling regulation of Ras superfamily of small guanosine triphosphatases. *Biochim. Biophys. Acta* 2009, 1791, 850-5; Limatola et al., Phosphatidic acid activation of protein kinase C-zeta overexpressed in COS cells: comparison with other protein kinase C isotypes and other acidic lipids. *Biochem. J.* 1994, 304 (Pt 3), 1001-8.) Cells have three mechanisms for producing PA: the conversion of phosphatidylcholine (PC) to PA and choline by phospholipase D (PLD) (Cummings et al., Phospholipase D/phosphatidic acid signal transduction: role and physiological significance in lung. *Mol. Cell Biochem.* 2002, 234-235, 99-109); the phosphorylation of diacylglycerol (DAG) to form PA through the action diacylglycerol kinase (DAGK) Cai et al., Diacylglycerol kinases as sources of phosphatidic acid. *Biochim. Biophys. Acta* 2009, 1791, 942-8); and the conversion of lysophosphatidic acid (LPA) to PA by the addition of an acyl group on its sn-2 position by the enzyme lysophosphatidic acid acyltransferase (LPAAT) (Leung, The structure and functions of human lysophosphatidic acid acyltransferases. *Front. Biosci.* 2001, 6, D944-53). A great deal is known concerning the roles of PLD and DAGK and their contribution to PA signaling in cancer, but most research involving LPAAT has focused on its role in lipid metabolism and membrane biosynthesis. Of the five human isoforms of LPAAT (α, β, γ, δ, and ε), only LPAAT-α and LPAAT-β have been studied in any detail. These two enzymes share 48% amino acid homology as well as four highly-conserved lysophospholipid acyltransferase (LPLAT) domains essential to their enzymatic function (Shindou et al., Acyl-CoA: lysophospholipid acyltransferases. *J. Biol. Chem.* 2009, 284, 1-5). Though LPAAT-α expression appears to be ubiquitous, expression of LPAAT-β is less so, with its highest levels in adipose, liver, heart, and pancreas tissue (Hollenback et al., Substrate specificity of lysophosphatidic acid acyltransferase beta—evidence from membrane and whole cell assays. *J. Lipid Res.* 2006, 47, 593-604; Agarwal et al., Congenital generalized lipodystrophy: significance of triglyceride biosynthetic pathways. *Trends Endocrinol. Metab.* 2003, 14, 214-21). Mutation of the LPAAT-β gene has been shown to be the cause of a human general lipodystrophy syndrome known as congenital generalized lipodystrophy 1 (CGL1) or Berardinelli-Seip Syndrome, a disorder which is marked by a nearly complete lack of body fat in those affected as well as severe insulin resistance (Agarwal et al., AGPAT2 is mutated in congenital generalized lipodystrophy linked to chromosome 9q34. *Nat. Genet.* 2002, 31, 21-3). In addition to this role in lipid metabolism, recent literature has also pointed to a role for LPAAT-β in cancer. Overexpression of LPAAT-β has been observed in lung, breast, colon, prostate, and glioma tissue compared to normal adjacent tissue as well as in osteosarcoma cells. (Bonham et al., id; Rastegar et al., Lysophosphatidic acid acyltransferase beta (LPAATbeta) promotes the tumor growth of human osteosarcoma. *PloS One* 2010, 5, e14182; Springett et al., Lysophosphatidic acid acyltransferase-beta is a prognostic marker and therapeutic target in gynecologic malignancies. *Cancer Res.* 2005, 65, 9415-25.)

Because of its implicated role in cancer signaling through its production of PA, both biochemical and pharmacologic inhibition of LPAAT-β has been studied in increasing detail. Knockdown of LPAAT-β by siRNA and pharmacologic means has been shown to have antiproliferative effects in a variety of cancer cell lines. (Bonham et al., id.; Springett et al., id.; Hideshima et al., Antitumor activity of lysophosphatidic acid acyltransferase-beta inhibitors, a novel class of agents, in multiple myeloma. *Cancer Res.* 2003, 63, 8428-36; La Rosee et al., Antileukemic activity of lysophosphatidic acid acyltransferase-beta inhibitor CT32228 in chronic myelogenous leukemia sensitive and resistant to imatinib. *Clin. Cancer Res.* 2006, 12, 6540-6; Pagel et al., Induction of apoptosis using inhibitors of lysophosphatidic acid acyltransferase-beta and anti-CD20 monoclonal antibodies for treatment of human non-Hodgkin's lymphomas. *Clin. Cancer Res.* 2005, 11, 4857-66.) Recently, it was reported that knockdown of LPAAT-β by siRNA led to inhibition of both anchorage-dependent and -independent pancreatic cancer cell growth, and that this inhibition was related to the ability of LPAAT-β to regulate the mTORC-1 and -2 kinase signaling pathways (Blaskovich et al., Lysophosphatidic Acid Acyltransferase Beta regulates mTOR signaling. *PloS One* 2013, 8, e78632).

Scheme 1. Structures of known LPAAT-β inhibitors 1-3

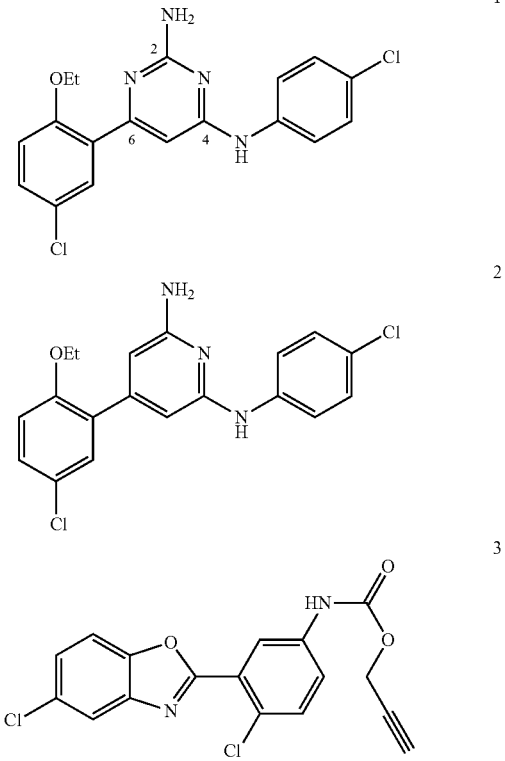

Previously, several LPAAT-β inhibitors have been reported, most notably, the 2-amino-4-anilino-6-arylpyrimidines 1 and its related pyridine 2 compounds show potent in vitro activity against LPAAT-β enzyme activity. (Gong et al., Synthesis and SAR of 2-arylbenzoxazoles, benzothiazoles and benzimidazoles as inhibitors of lysophosphatidic acid acyltransferase-beta. *Bioorg. Med. Chem. Lett.* 2004, 14, 1455-9; Hong et al., Diamino-C,N-diarylpyridine positional isomers as inhibitors of lysophosphatidic acid acyltransferase-beta. *Bioorg. Med. Chem. Lett.* 2005, 15, 4703-7.) Selected compounds of these pharmacophores were demonstrated to have inhibitory activity against anchorage-dependent and -independent growth of gynecological (Springett et al. id.), leukemic (La Rosee et al., id.), and multiple myeloma (Hideshima et al., id.) cancer cells. In addition, these compounds were shown to induce apoptosis and to have antitumor activity and increased survival of nude mouse human ovarian xenografts. Additionally the 2-arylbenzoxazole 3, and its related benzothiazole and benzimadazole were shown to have potent anti-enzymatic activity against LPAAT-β in vitro. (Gong et al., Synthesis, SAR, and antitumor properties of diamino-C,N-diarylpyrimidine positional isomers: inhibitors of lysophosphatidic acid acyltransferase-beta. *Bioorg. Med. Chem. Lett.* 2004, 14, 2303-8). Disclosed herein are thiosemicarbazone-based LPAAT-β inhibitors, identified through high throughput screening, with potent activity against LPAAT-β in vitro and having low micromolar anti-proliferative activity against pancreatic cancer cell growth.

SUMMARY

Disclosed are compounds which show inhibitory activity against LPAAT-β in a screening assay, and have confirmed inhibition of LPAAT-β directly in a secondary TLC assay. 5-halogenated, 3-allyl derivatives of F0777-0574 were identified that show low micromolar activity against LPAAT-β in vitro with micromolar activity against the proliferation of pancreatic cancer cell lines in culture. These compounds also show synergy with FDA-approved drugs used clinically. These results further validate LPAAT-β as a therapeutic target.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIGS. 10A-10C show that SiRNA knockdown of LPAAT-beta inhibits soft agar colony formation. Note that in panel B and C in Panc-1 and MiaPaca2 respectively, the effect on anchorage independent growth of siRNA knockdown of LPAAT-beta is almost as great as the effect of knockdown of Kras. This suggests that Kras driven proliferation may be partly dependent on LPAAT-beta.

FIG. 14 shows that adding PA directly to cells increased the quantity of active GTP bound RalA by 15-20%. Inhibiting cellular PA levels by siRNA to LPAAT-beta reduces active GTP bound RalA by about 15%. This is the same degree of inhibition seen with inhibition of Kras by siRNA.

FIG. 15 shows selective data for library screening of LPAAT-beta inhibition.

DETAILED DESCRIPTION

Figure 1:
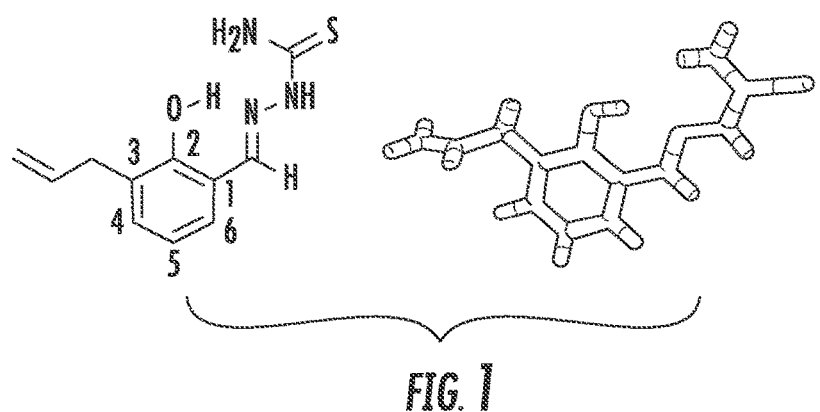
FIG. 1 is the structure of 6a and its crystal structure.

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

CHEMICAL DEFINITIONS

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NZ^1Z^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1$O$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1$C(O)$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Screening with a modified screening assay in 96-well plate format for LPAAT-β enzymatic activity was performed as reported by Aguado and Campbell (Aguado et al., Characterization of a human lysophosphatidic acid acyltransferase that is encoded by a gene located in the class III region of the human major histocompatibility complex. *J. Biol. Chem.* 1998, 273, 4096-105).

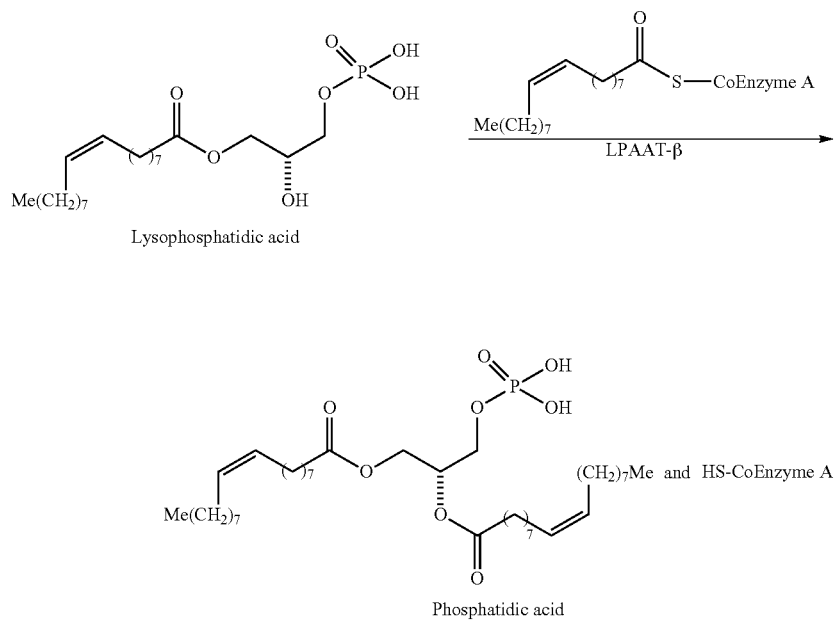

Scheme 2. Transformation of oleyl-Lysophosphatidic acid into oleyl-Phosphatidic acid The assay utilizes full-length, recombinant, baculovirus-produced LPAAT-β, which catalyzes the production of dioleoyl-lysophosphatidic acid (PA) from the enzymatic substrates oleoyl-lysophosphatidic acid (LPA) and oleoyl-coenzyme A (Scheme 2). The ability of the compound to inhibit the LPAAT-β activity was assayed by the colorimetric measurement of the reaction of the free thiol group of the released coenzyme A with Ellman's reagent [5,5'-dithiobis-(2-nitrobenzoic acid) or DTNB] (Riener et al., Quick measurement of protein sulfhydryls with Ellman's reagent and with 4,4'-dithiodipyridine. *Anal. Bioanal. Chem.* 2002, 373, 266-76). To eliminate nonspecific compounds identified from the DTNB plate assay, activity was confirmed using a secondary thin layer chromatography (TLC) assay that directly measures the fluorescent PA produced from oleoyl-LPA and a fluorochrome-labeled (NBD) palmitoyl-coenzyme A. The screen of the libraries identified several hits with $IC_{50}$ ranging from 15 μM to 100 nM. A hit identified from the Life Chemicals library 6a ($IC_{50}$ 100 nM) was selected for further investigation.

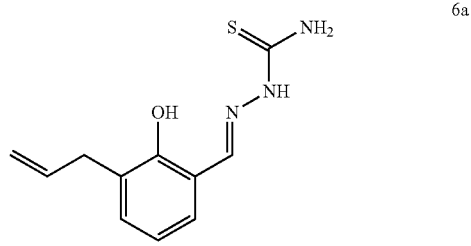 [SMILES: C=CCc1cccc(/C=N/NC(N)=S)c1O]

This hit 6a was synthesized by the condensation of 3-allyl-2-hydroxybenzaldehyde and thiosemicarbazide and screened for its inhibition of LPAAT-β. The sample of 6a had an $IC_{50}$ of 0.86±0.52 μM. The structure of 6a was confirmed by full structural characterization by $^1H$ and $^{13}C$ NMR and mass spectroscopy analysis. A single crystal X-ray structure of 6a showed that the hydrazine is configured E, and the phenolic OH is hydrogen bonded to the terminal nitrogen of the carbazone unit as shown in FIG. 1. Semicarbazones have been found to be useful scaffolds for anticancer drug discovery (Kalinowski et al., Thiosemicarbazones: the new wave in cancer treatment. *Future Med. Chem.* 2009, 1, 1143-51; Yu et al., Thiosemicarbazones from the old to new: iron chelators that are more than just ribonucleotide reductase inhibitors. *J. Med. Chem.* 2009, 52, 5271-94).

A focused library of thiosemicarbazones derivatives related to 6a was then prepared to investigate the influence upon LPAAT-β inhibition of the group at the 3 position adjacent to the hydroxyl group (i.e., $R^1$). The first nine members of the library 6a-i were synthesized by heating readily available 3-substituted salicylaldehydes 5a-i with thiosemicarbazide in a microwave reactor (method b) as shown in Scheme 3. The salicylaldehydes bearing an ethyl, isopropyl, phenyl and cyclohexyl group (5j, 5k, 5m, and 5n) were prepared from their corresponding phenols by treatment with paraformaldehyde and magnesium chloride (Hansen et al., Ortho-Formylation of Phenols; Preparation of 3-Bromosalicylaldehyde. *Org. Synth.* 2005, 82, 64-68; Hansen et al., Discussion Addendum for Ortho-Formylation of Phenols; Preparation of 3-Bromosalicylaldehyde. *Org. Synth.* 2012, 89, 220-229). The 3-propylsalicylaldehyde 5l was prepared by hydrogenation of the 3-allylsalicylaldehyde 5a (method c). This set of salicylaldehydes 5j-n then provided the corresponding thiosemicarbazones 6j-n using method b.

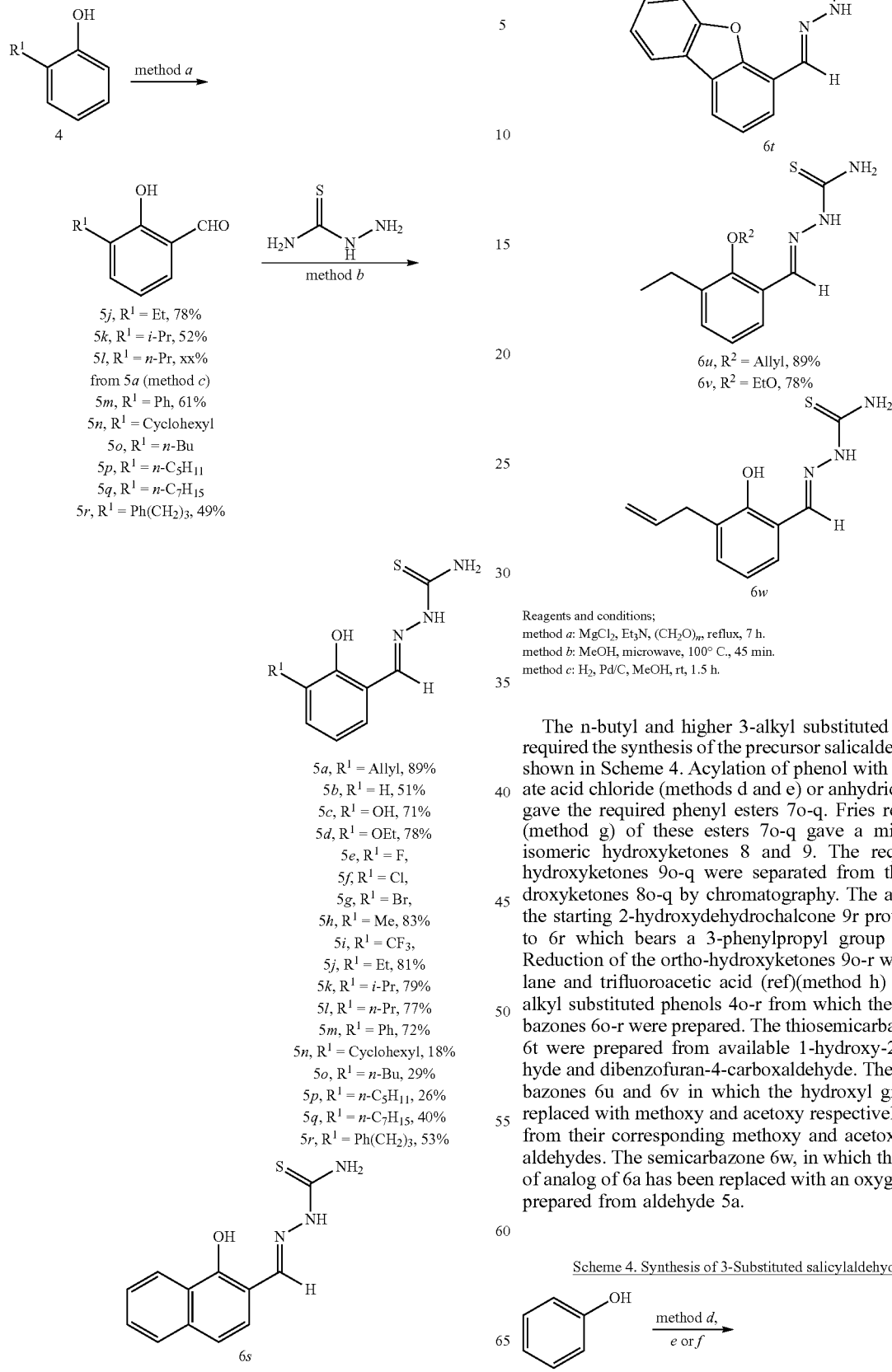

Reagents and conditions;
method a: MgCl$_2$, Et$_3$N, (CH$_2$O)$_n$, reflux, 7 h.
method b: MeOH, microwave, 100° C., 45 min.
method c: H$_2$, Pd/C, MeOH, rt, 1.5 h.

The n-butyl and higher 3-alkyl substituted analogs 6o-r required the synthesis of the precursor salicaldehydes 5o-r as shown in Scheme 4. Acylation of phenol with the appropriate acid chloride (methods d and e) or anhydride (method f) gave the required phenyl esters 7o-q. Fries rearrangement (method g) of these esters 7o-q gave a mixture of the isomeric hydroxyketones 8 and 9. The required ortho-hydroxyketones 9o-q were separated from their para-hydroxyketones 8o-q by chromatography. The availability of the starting 2-hydroxydehydrochalcone 9r provided a route to 6r which bears a 3-phenylpropyl group (Scheme 6). Reduction of the ortho-hydroxyketones 9o-r with triethylsilane and trifluoroacetic acid (ref)(method h) provided the alkyl substituted phenols 4o-r from which the thiosemicarbazones 6o-r were prepared. The thiosemicarbazones 6s and 6t were prepared from available 1-hydroxy-2-naphthaldehyde and dibenzofuran-4-carboxaldehyde. The thiosemicarbazones 6u and 6v in which the hydroxyl group of 6j is replaced with methoxy and acetoxy respectively were made from their corresponding methoxy and acetoxy containing aldehydes. The semicarbazone 6w, in which the sulfur atom of analog of 6a has been replaced with an oxygen atom, was prepared from aldehyde 5a.

Scheme 4. Synthesis of 3-Substituted salicylaldehydes 4j-m.

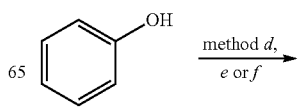

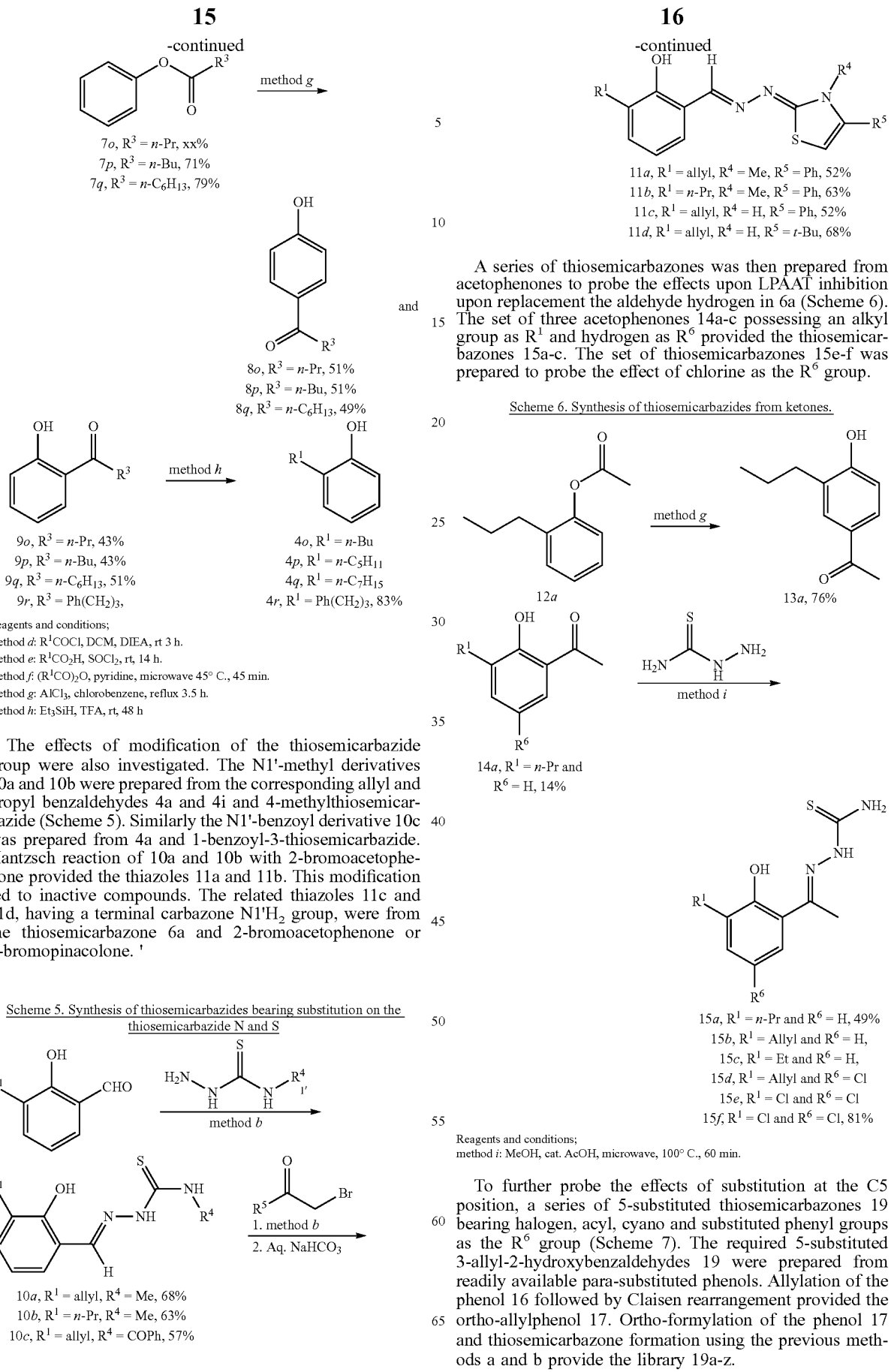

The effects of modification of the thiosemicarbazide group were also investigated. The N1'-methyl derivatives 10a and 10b were prepared from the corresponding allyl and propyl benzaldehydes 4a and 4i and 4-methylthiosemicarbazide (Scheme 5). Similarly the N1'-benzoyl derivative 10c was prepared from 4a and 1-benzoyl-3-thiosemicarbazide. Hantzsch reaction of 10a and 10b with 2-bromoacetophenone provided the thiazoles 11a and 11b. This modification led to inactive compounds. The related thiazoles 11c and 11d, having a terminal carbazone N1'H$_2$ group, were from the thiosemicarbazone 6a and 2-bromoacetophenone or 1-bromopinacolone. '

A series of thiosemicarbazones was then prepared from acetophenones to probe the effects upon LPAAT inhibition upon replacement the aldehyde hydrogen in 6a (Scheme 6). The set of three acetophenones 14a-c possessing an alkyl group as R$^1$ and hydrogen as R$^6$ provided the thiosemicarbazones 15e-f. The set of thiosemicarbazones 15e-f was prepared to probe the effect of chlorine as the R$^6$ group.

To further probe the effects of substitution at the C5 position, a series of 5-substituted thiosemicarbazones 19 bearing halogen, acyl, cyano and substituted phenyl groups as the R$^6$ group (Scheme 7). The required 5-substituted 3-allyl-2-hydroxybenzaldehydes 19 were prepared from readily available para-substituted phenols. Allylation of the phenol 16 followed by Claisen rearrangement provided the ortho-allylphenol 17. Ortho-formylation of the phenol 17 and thiosemicarbazone formation using the previous methods a and b provide the library 19a-z.

Scheme 7. Synthesis of 5-substituted semithiocarbazides.

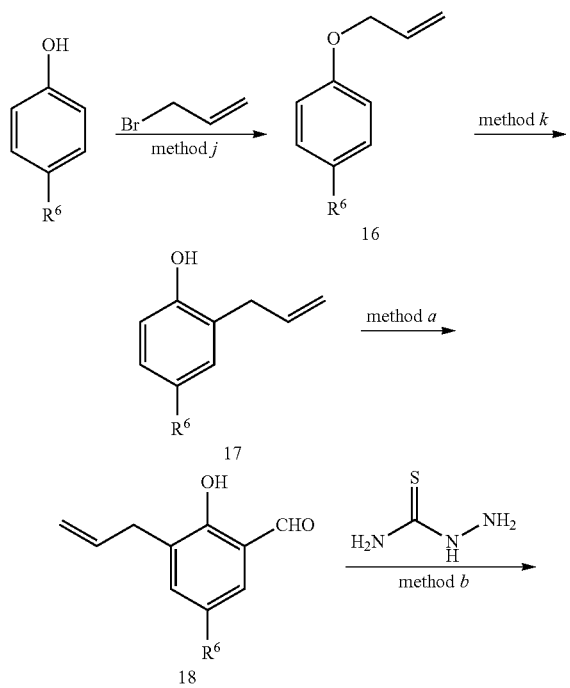

19a, R⁶ = Cl
19b, R⁶ = F
19c, R⁶ = Br
19d, R⁶ = CN
19e, R⁶ = Et
19f, R⁶ = n-Pr
19g, R⁶ = i-Pr
19h, R⁶ = n-Bu
19i, R⁶ = t-Bu
19j, R⁶ = n-Pentyl
19k, R⁶ = n-Hexyl
19l, R⁶ = COMe
19m, R⁶ = CH₂CO₂Me

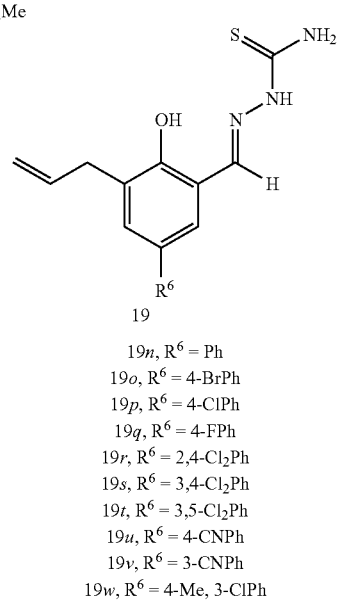

19n, R⁶ = Ph
19o, R⁶ = 4-BrPh
19p, R⁶ = 4-ClPh
19q, R⁶ = 4-FPh
19r, R⁶ = 2,4-Cl₂Ph
19s, R⁶ = 3,4-Cl₂Ph
19t, R⁶ = 3,5-Cl₂Ph
19u, R⁶ = 4-CNPh
19v, R⁶ = 3-CNPh
19w, R⁶ = 4-Me, 3-ClPh

Reagents and conditions;
method j: Cs₂CO₃, MeCN, 100° C., 45 min.
method k: microwave, 225° C.

Disclosed herein are compounds having Formula I.

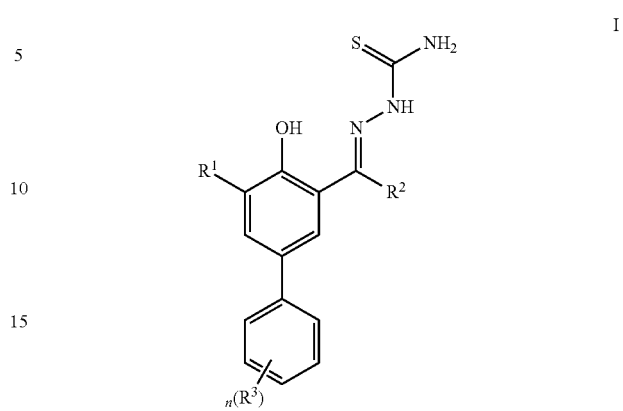

$R^1$ is F, Cl, Br, $CF_3$, or $C_{1-5}$ alkyl, or $C_{2-5}$ alkenyl,
$R^2$ is H or optionally substituted $C_{1-6}$ alkyl or phenyl; and
n is 1, 2, 3, 4 or 5; and
each $R^3$ is, independent of any other, F, Cl, Br, OH, CN, $NH_2$, optionally substituted $C_{1-8}$ alkyl, $C_{1-8}$ alkenyl, $OC_1$-$C_8$ alkyl, $OC_{2-8}$ alkenyl, $NHC_1$-$C_8$ alkyl, $NHC_2$-$C_8$ alkenyl, $C_{5-6}$ cycloalkyl, phenyl, $COC_{1-8}$ alkyl, $COC_{5-6}$ cycloalkyl, or CO phenyl; $CONHC_{1-8}$ alkyl, $CONHC_{5-6}$ cycloalkyl, or CONHphenyl; or $R^2$ and $R^3$ can form a fused aryl or heteroaryl;
wherein optional substituents are selected from F, Cl, Br, OH, CN, $C_{1-8}$ alkyl, $OC_{1-8}$ alkyl, phenyl, CN, $C_{1-4}$ haloalkyl, or a pharmaceutical acceptable salt thereof.

In certain aspects, $R^1$ is a C2-4 alkyl. In other examples, $R^1$ is propenyl.

In other examples, $R^2$ is H. In other examples $R^2$ is methyl.

In other examples, n can be 2. For example, each $R^3$ can be at the 2 or 6 position of the phenyl ring, the 2 and 5 position, or the 2 and 4, or the 2 and 3 position. Alternatively, each $R^3$ can be at the 3 and 6 position, the 3 and 5 position, or the 3 and 4 position.

In still other examples, n can be 3. For example, each $R^3$ can be at the 2, 3 and 6 position, the 2, 3, and 5 position, the 2, 3, and 4 position, the 3, 4, and 6 position, or the 3, 4, and 5 position.

In other examples, n is 2 and each $R^3$ is chosen from F, Cl, Br, and CN.

Methods of Use

Further provided herein are methods of treating or preventing cancer in a subject, comprising administering to the subject an effective amount of a compound or composition as disclosed herein. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid.

Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are compositions comprising the disclosed compounds of Formula I and another anti-cancer compound. Examples of some chemotherapeutic agents that can be used according to the disclosed methods are 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Oraped, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR.

Kits

The disclosed subject matter also concerns a packaged dosage formulation comprising in one or more containers at least one inhibitor compound or composition disclosed herein, e.g., any compound of Formula I. A packaged dosage formulation can optionally comprise in one or more containers a pharmaceutically acceptable carrier or diluent.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

The structures of all the final compounds were confirmed by analysis of NMR and mass spectroscopic data. In addition, HPLC methods (typically two methods) were used to determine the purity (generally >96%) of the compounds. All compounds were screened against LPAAT-β. $IC_{50}$ values were generally determined only for compounds that inhibited LPAAT-β activity by at least 40% at a compound concentration of 10 µM. The results are summarized in Tables 1-5 and discussed below.

Comparative Compounds

The initial hit 6a displayed good activity against LPAAT-β ($IC_{50}$ 0.86±0.52 µM) as measured in the DTNB assay (Table 1). The thiosemicarbazone 6b ($R^1$=H) derived from salicylaldehyde was inactive in both assays, clearly indicating that the substituent at the 3 position significantly effects LPAAT-β inhibitory activity. Both the hydroxy and ethoxy containing thiosemicarbazones 6c and 6d were also inactive. The halogen containing thiosemicarbazones 6e-6g were less active than the hit 6a. The activity showed a small increase with increasing size and decreasing electronegativity of the halogen. The effects of chain length of a hydrocarbon group at the 3 position revealed an important structure activity relationship. The methyl homolog 6h is considerably less active than 6a further indicating that a small group reduces LPAAT-β inhibitory activity. However, both the ethyl and n-propyl homologs 6j and 6k had activities ($IC_{50}$ 0.85±0.56 and 0.79±0.53 µM respectively) similar to that of 6a ($IC_{50}$ 0.86±0.52 µM). The n-butyl derivative 6o ($IC_{50}$ 6.7±1.6 µM) is less active than the propyl analog ($IC_{50}$ 0.93±0.37 µM). Thiosemicarbazones with larger $R^1$ groups such as n-pentyl (6p), n-heptyl (6q) and 3-phenylpropyl (6r) analogs are effectively inactive ($IC_{50}$>100 µM). There is a pattern across the series H, Me, Et, Pr, Bu, n-pentyl and n-heptyl as shown by the activities >100, 7.5, 0.86, 0.79, >100, >100, >100. The ethyl and propyl groups at position 3 give rise to the best activity. The activities of 6j and 6k ($IC_{50}$ 48±15 and 19±11 µM respectively) also were similar to that of 6a ($IC_{50}$ 33±13 µM) in the TLC assay. Branching of the alkyl group proved detrimental to activity; the iso-propyl containing thiosemicarbazone 6l ($IC_{50}$ 13±8.4 µM) is significantly less active than the n-propyl analog 6k ($IC_{50}$ 0.79±0.53 µM). Further confirmation that a small alkyl group at position 3 is optimal was provided by the phenyl ($IC_{50}$ 40±10 µM) and cyclohexyl ($IC_{50}$>100 µM) analogs 6m and 6n. The naphthyl thiosemicarbazone 6s ($IC_{50}$ 6.4±4.7 µM) retains some activity but is significantly poorer than the ethyl containing analog 6j ($IC_{50}$ 0.85±0.56 µM). The thiosemicarbazone 6t, which is structurally related to the 3-phenyl derivative 6m ($IC_{50}$ 40±10 µM), was inactive, perhaps indicating that the 2-hydroxyl was important for activity. This was indeed shown to be the case, since the analogs 6u ($IC_{50}$>100 µM) and 6v ($IC_{50}$ 66±4.8 µM), in which the hydroxy group of 6a has been substituted by an acetoxy and methoxy group respectively are significantly less active.

TABLE 1

Activities of thiosemicarbazones 6 against LPAAT-β in the DTNB and TLC assays.

| Compound | | $R^1$ | $IC_{50}$ (μM) (DTNB assay) | $IC_{50}$ (μM) (TLC assay) |
|---|---|---|---|---|
| 6 | 6a | Allyl | 0.86 ± 0.52 | 33 ± 13 |
| | 6b | H | >100 | >100 |
| | 6c | HO | >100 | >10 |
| | 6d | EtO | >100 | >10 |
| | 6e | F | 4.3 ± 3.6 | >10 |
| | 6f | Cl | 2.0 ± 1.2 | >10 |
| | 6g | Br | 1.5 ± 1.4 | >10 |
| | 6h | Me | 7.5 ± 1.8 | >10 |
| | 6i | $CF_3$ | 7.0 ± 2.0 | >10 |
| | 6j | Et | 0.85 ± 0.56 | 48 ± 15 |
| | 6k | n-Pr | 0.79 ± 0.53 | 19 ± 11 |
| | 6l | i-Pr | 13 ± 8.4 | 30 |
| | 6m | Ph | 40 ± 10 | >10 |
| | 6n | Cyclohexyl | >100 | >10 |
| | 6o | n-Bu | >100 | >10 |
| | 6p | n-$C_5H_{11}$ | >100 | >10 |
| | 6q | n-$C_7H_{15}$ | >100 | 9.7 |
| | 6r | $Ph(CH_2)_3$ | | |

6s
$IC_{50}$ (DTNB) 6.4 ± 4.7 μM

6t
$IC_{50}$ (DTNB) >100 μM

6u, $R^2$ = Allyl,
$IC_{50}$ (DTNB) >100 μM
6v, $R^2$ = Me,
$IC_{50}$ (DTNB) 66 ± 4.8 μM 6w
$IC_{50}$ (DTNB) >100 μM The semicarbazone 6w (Table 1) is inactive, indicating that the thiourea-like group is important for activity. Thiosemicarbazide, the reagent used to make the thiosemicarbazones, is not by itself active. Substitution at the terminal $N1'H_2$ group was investigated next (numbered according to structure 10, Table 2). The allyl and propyl-containing N1'-methyl derivatives 10a and 10b (Scheme 5) were less active ($IC_{50}$ 3.9±2.3 μM and $IC_{50}$ 14±12 μM respectively) than their non-methyl analogs 6a $IC_{50}$ 0.86±0.52 μM) and 6k ($IC_{50}$ 14±12 μM) (Table 2). The related N1'-benzoyl derivative 10c was inactive. The thiazoles 11a-d, derived from their parent thiosemicarbazones 10a, 10b and 6a were also inactive (Table 2). This indicates that modification at the N1' position is unlikely to give rise to improved potency.

TABLE 2

Activities of thiosemicarbazones 10 and 11 against LPAAT-β in the DTNB and TLC assays.

| Compound | | $R^1$ | $R^4$ | $R^5$ | $R^6$ | $IC_{50}$ (μM) (DTNB assay) | $IC_{50}$ (μM) (TLC assay) |
|---|---|---|---|---|---|---|---|
| 10 | 10a | Allyl | Me | — | — | 3.9 ± 2.3 | >10 |
| | 10b | n-Pr | Me | — | — | 14 ± 12 | >10 |
| | 10c | n-Pr | COPh | — | — | >100 | >10 |
| 11 | 11a | Allyl | Me | Ph | | >100 | >10 |
| | 11b | n-Pr | Me | Ph | | >100 | >10 |
| | 11c | Allyl | H | Ph | | >100 | >10 |
| | 11d | Allyl | H | t-Bu | | >100 | >10 |

Exemplary Compounds

The effect of substitution at the imine-like position C5' was investigated. The thiosemicarbazone 15a, prepared from the acetophenone 14a (Scheme 6) was significantly active (IC$_{50}$ 0.65±0.42 μM) (Table 3). The activity of 15a was comparable to that of its C5' hydrogen bearing analog 6k (IC$_{50}$ 0.79±0.53 μM). The H to Me switch at the C5' position was also tolerated when the R$^1$ group was allyl in 15b (IC$_{50}$ 0.52±0.25 μM) and ethyl in 15c (IC$_{50}$ 0.73±0.76 μM). The thiosemicarbazones 15d-f with a C5' methyl group and a chlorine atom as the R$^6$ group were also significantly active.

TABLE 3

Activities of thiosemicarbazones 15 against LPAAT-β in the DTNB and TLC assays.

| Compound | R$^1$ | R$^4$ | R$^5$ | R$^6$ | IC$_{50}$ (μM) (DTNB assay) | IC$_{50}$ (μM) (TLC assay) |
|---|---|---|---|---|---|---|
| 15a | n-Pr | — | — | H | 0.65 ± 0.42 | 35 ± 18 |
| 15b | Allyl | — | — | H | 0.52 ± 0.25 | >10 |
| 15c | Et | — | — | H | 0.73 ± 0.76 | >10 |
| 15d | Allyl | — | — | Cl | 0.20 ± 0.12 | 32 ± 25 |
| 15e | H | — | — | Cl | 2.8 ± 4.3 | >10 |
| 15f | Cl | — | — | Cl | 0.27 ± 0.12 | >10 |

15

The effect of an R$^6$ substitution was investigated in aldehyde-derived thiosemicarbazones 19. The in vitro LPAAT-β inhibitory values are shown in Table 4. The chlorine-containing thiosemicarbazone 19a was significantly more active (IC$_{50}$ 0.17±0.09 μM) than its hydrogen-containing analog 6a (IC$_{50}$ 0.86±0.52 μM) in the DTNB assay. This improved potency was also reflected in the LPAAT-β TLC assay (19a IC$_{50}$ 3.3±1.2 μM and 6a IC$_{50}$ 33±13 μM). The bromine analog 19b was similarly potent in both assays [IC$_{50}$ 0.10±0.03 μM (DTNB) and IC$_{50}$ 4.1±2.2 μM (TLC)]. The fluorine-containing thiosemicarbazone 19b was a little less active than 6a in the TDNB assay (IC$_{50}$ 0.24±0.14 μM); it was significantly less active in the TLC assay (IC$_{50}$ 24±10 μM). The alkyl series of 19e-19l provided compounds with similar potency as 19a. The derivative with the longest chain in the series, the n-hexyl thiosemicarbazone 19k is much less active than 19a in the DTNB assay (IC$_{50}$ 17±7.3 μM) and nearly two-fold less active in the TLC assay (IC$_{50}$ 3.2±1.6 μM). An acetyl group as the R$^6$ residue in 19l diminishes the LPAAT-β inhibitory activity (IC$_{50}$ 2.67±0.25 μM in the DTNB and >10 μM in the TLC assay). Similarly the methyl ester group attached to the C5 methylene group of 19n reduced activity (IC$_{50}$ 1.15±1.04 μM) in the DTNB assay relative to 19a. An aryl group as the R$^6$ residue for the series 19n-w results in compounds with activities similar to those of the alkyl substituted series 19e-19l. For example the phenyl substituted thiosemicarbazone 19n is as potent as 19a in the DTNB assay (IC$_{50}$ 0.19±0.10 μM) and a little less active in the TLC assay (IC$_{50}$ 5.7±2.5 μM). The presence of halogens at the 4-position of the aryl group did not make a significant difference in the series 19p-r. Similarly, the 3,4-dichloro substituted thiosemicarbazone 19s (IC$_{50}$ 0.36±0.10 μM in the DTNB and 2.4±0.7 μM in the TLC assay) also had activities similar to 19a. Its isomer, the 3,5-dichloro containing thiosemicarbazone 19t was less active in both assays (IC$_{50}$ 0.57±0.27 μM in the DTNB and 17±7.3 μM in the TLC assay). The presence of a methyl group at the 4-position in 19w (IC$_{50}$ 0.67±0.16 μM) reduces activity in the DTNB assay compared to 19u (IC$_{50}$ 0.36±0.10 μM). Overall in this series substitution at the C5 position has resulted in compounds with activity in both assay formats significantly greater than the activity of 6a.

TABLE 4

Activities of thiosemicarbazones 19 against LPAAT-β in the DTNB and TLC assays.

| Compound | | $R^6$ | $IC_{50}$ (μM) (DTNB assay) | $IC_{50}$ (μM) (TLC assay) |
|---|---|---|---|---|
| | 19a | Cl | 0.17 ± 0.09 | 3.3 ± 1.2 |
| | 19b | F | 0.24 ± 0.14 | 24 |
| | 19c | Br | 0.10 ± 0.03 | 4.1 ± 2.2 |
| | 19d | CN | 0.46 ± 0.34 | >10 |
| | 19e | Et | 0.20 ± 0.08 | 1.9 ± 0.3 |
| | 19f | n-Pr | 0.27 ± 0.12 | 2.4 ± 1.3 |
| | 19g | i-Pr | 0.16 ± 0.06 | 1.4 ± 1.1 |
| | 19h | n-Bu | 0.16 ± 0.07 | 1.4 ± 1.1 |
| | 19i | t-Bu | 0.31 ± 0.05 | 1.3 ± 0.6 |
| | 19j | n-Pentyl | 0.19 ± 0.09 | 3.2 ± 2.6 |
| | 19k | n-Hexyl | 0.24 ± 0.17 | 5.2 ± 2.1 |
| | 19l | COMe | 2.67 ± 0.25 | >10 |
| | 19m | $CH_2CO_2Me$ | 1.15 ± 1.04 | >10 |
| | 19n | Ph | 0.19 ± 0.10 | 5.7 ± 2.5 |
| | 19o | 4-BrPh | 0.18 ± 0.07 | 4.2 ± 1.2 |
| | 19p | 4-ClPh | 0.32 ± 0.07 | 2.5 ± 1.4 |
| | 19q | 4-FPh | 0.29 ± 0.06 | 5.1 ± 3.0 |
| | 19r | 2,4-$Cl_2$Ph | 0.52 ± 0.23 | 2.1 ± 0.9 |
| | 19s | 3,4-$Cl_2$Ph | 0.36 ± 0.10 | 2.4 ± 0.7 |
| | 19t | 3,5-$Cl_2$Ph | 0.57 ± 0.27 | 17 ± 7.3 |
| | 19u | 4-CNPh | 0.40 ± 0.19 | 1.0 ± 0.9 |
| | 19v | 3-CNPh | 0.28 ± 0.02 | >10 |
| | 19w | 4-Me,3-ClPh | 0.67 ± 0.16 | 9.2 ± 4.2 |

Inhibition of Pancreatic Cell Proliferation.

Figure 2:
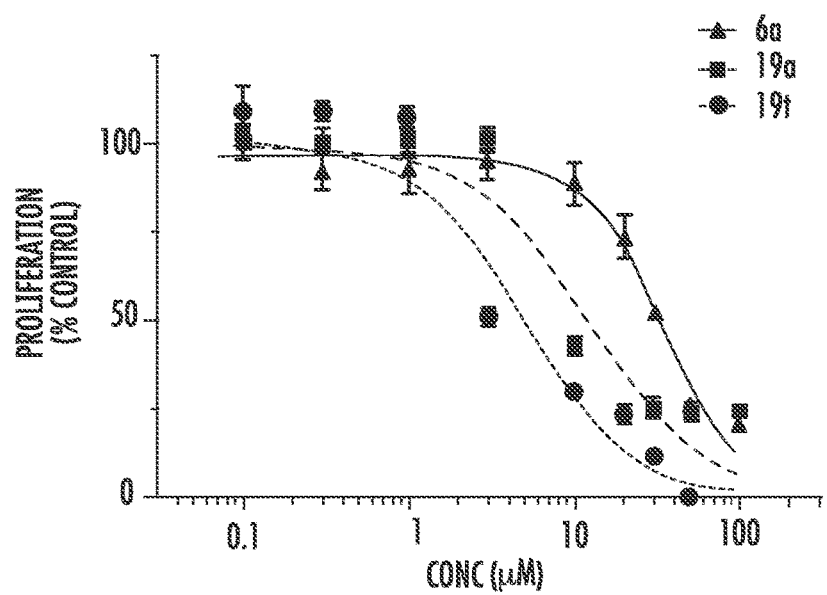
FIG. 2 is a graph of the cell growth inhibitory properties of compounds 6a, 19a and 19t against MiaPaCa2 human pancreatic cancer cells.
Figure 3:
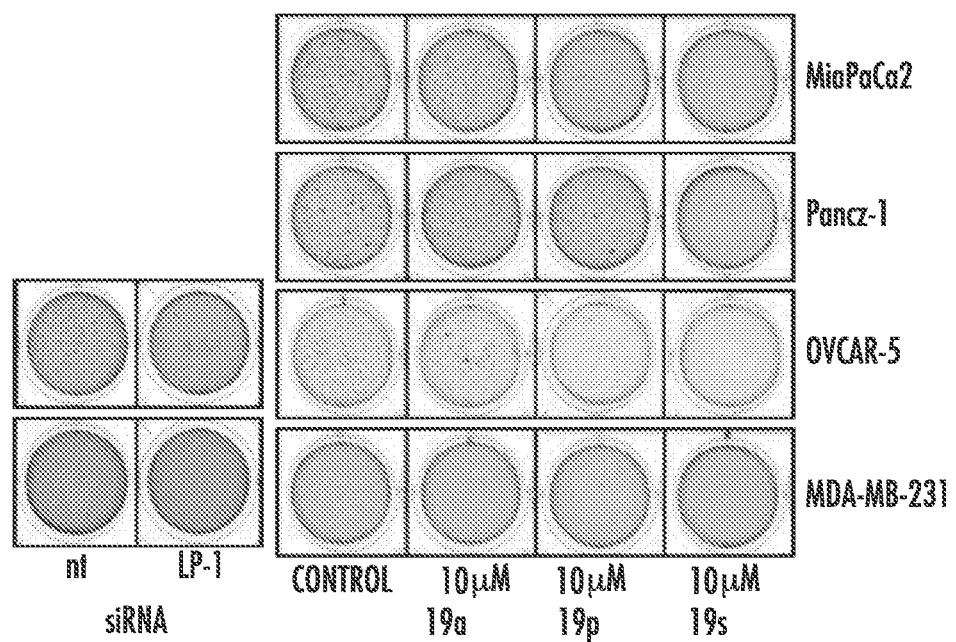
FIG. 3. LPAAT-β inhibitors block anchorage-independent growth of cancer cell lines. Human pancreatic (MiaPaCa2 and Panc-1), ovarian (OVCAR-5) and breast cancer (MDAMB-231) cells were plated into 3% agar containing LPAAT-β inhibitors and allowed to grow for 2-4 weeks in the presence of the compounds. Lead inhibitor 19s shows potent inhibition of the anchorage-independent growth in each of these cancer cell lines. This effect of the small molecules is similar to the effect of knockdown with LPAAT-β siRNA (nt, non-targeting; LP-1, LPAAT-β).
Figure 4:
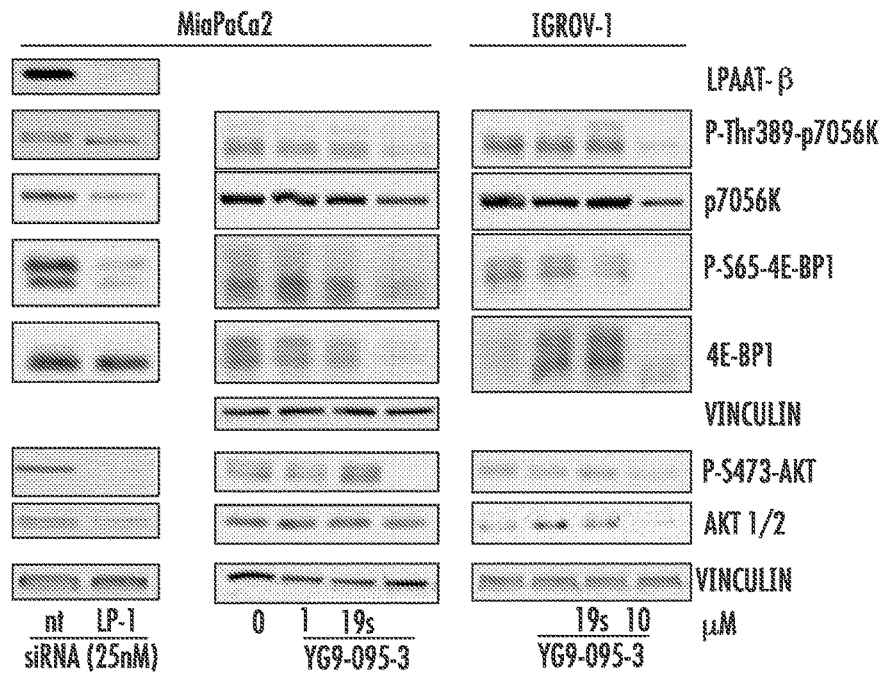
FIG. 4. Inhibition of mTOR effector protein phosphorylation by LPAAT-β inhibitor. To test if 19s is also able to inhibit mTOR-related signaling, pancreatic (MiaPaCa2) and ovarian (IGROV-1) cells were treated with increasing concentrations of 19s and used Western blotting to determine whether there was inhibition of mTOR effector protein phosphorylation. Treatment with the LPAAT-β inhibitor 19s shows a similar pattern to the inhibition of mTOR effector protein phosphorylation as seen with knockdown of LPAAT-β expression by siRNA. Treatment with 10 µM of 19s resulted in inhibition of 43%, 76%, and 88% of P-p70, P-4E-BP1, and P-AKT in MiaPaCa2, and 25%, 45%, and 5% in IGROV-1.
Figure 5A:
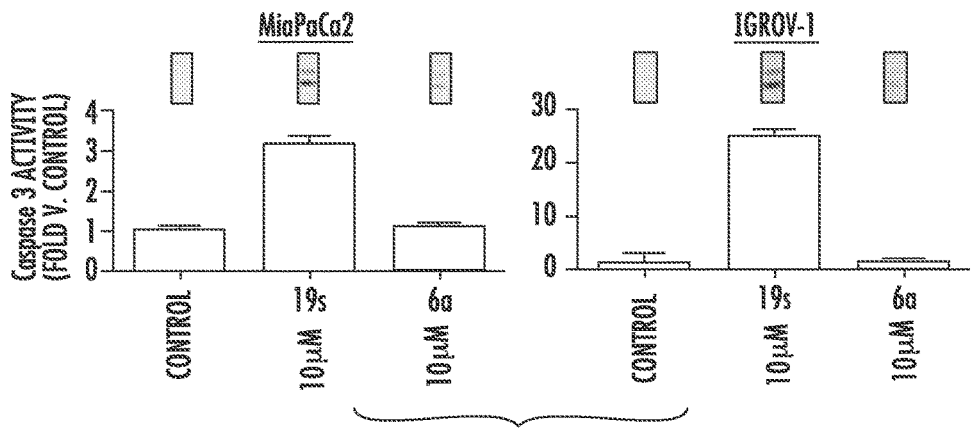
FIGS. 5A-5B. Induction of apoptosis with 19s treatment in pancreatic and ovarian cancer cell lines. Human pancreatic (MiaPaCa2) and ovarian (IGROV-1) cells were treated for 48 hr with LPAAT-b inhibitors then harvested and the samples assayed for their ability to cleave a fluorescent Caspase 3 specific substrate, Av-DEVD-AMC (A) In addition, the samples were run on SDS-PAGE gels and Western blotted to assess the presence of the activated form of Caspase 3 (inset). MiaPaCa2 cells show 3.5-fold and IGROV-1 cells show 25-fold activation of Caspase 3 activity after treatment with 19s compared to a vehicle-treated control sample. (B) PARP cleavage in MiaPaCa2 cells treated for 72 hr with 10 µM 19s and 19p.
Figure 5B:
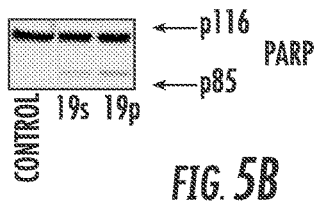
Figure 6:
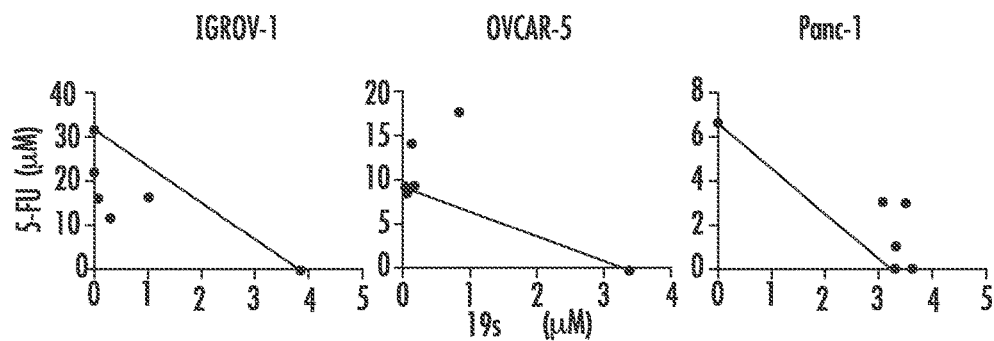
FIG. 6. Synergistic effect of YG9-095-3 with 5-FU in IGROV-1 ovarian cancer cells. Human ovarian and pancreatic carcinoma cell lines (IGROV-1 and OVCAR-5; Panc-1) were treated for 72 hr with 19s, 5-FU, and the two drugs in simultaneous combination. After 72 hr, results for cellular proliferation were obtained using Alamar blue, and isobolograms of $IC_{50}$ value were plotted to determine if a synergistic treatment effect occurred with the combination of these drugs. 19s and 5-FU work in a moderately synergistic manner to inhibit cellular proliferation of IGROV-1 cells. However, in OVCAR-5 cells, at low concentration there appears to be an additive effect of the two drugs on proliferation, but the effect becomes antagonistic at the higher concentrations of YG9-095-3. In Panc-1, the combination of the drugs is mildly additive to antagonistic. These results indicate that synergistic combinations of 5-FU and 19s may be cell type or perhaps sequence specific.
Figure 7:
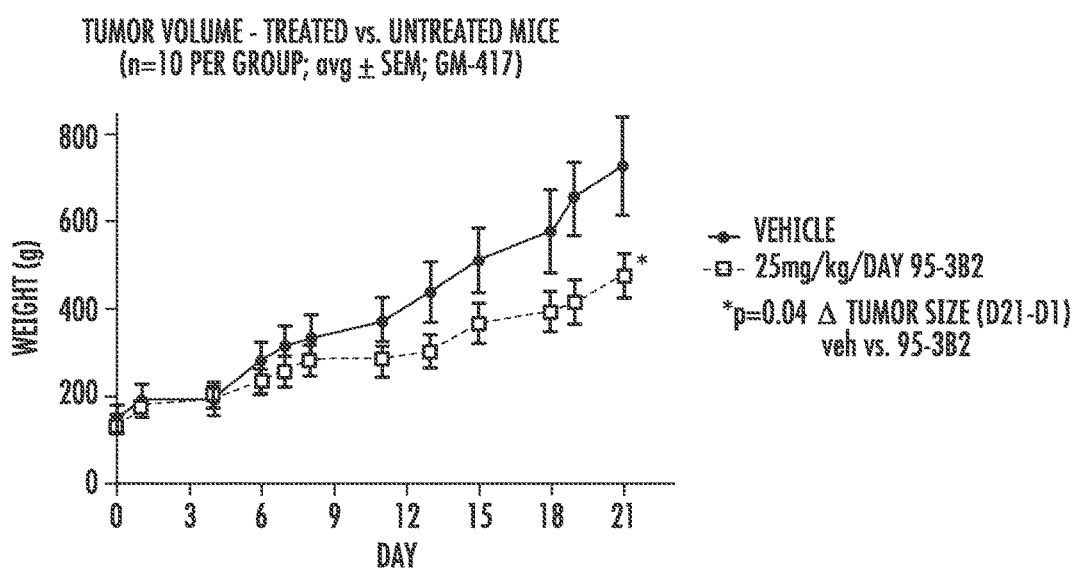
FIG. 7 is a graph of tumor volume for treated versus untreated mice (n=10 per group; average ± SEM; GM-417).
Figure 8:
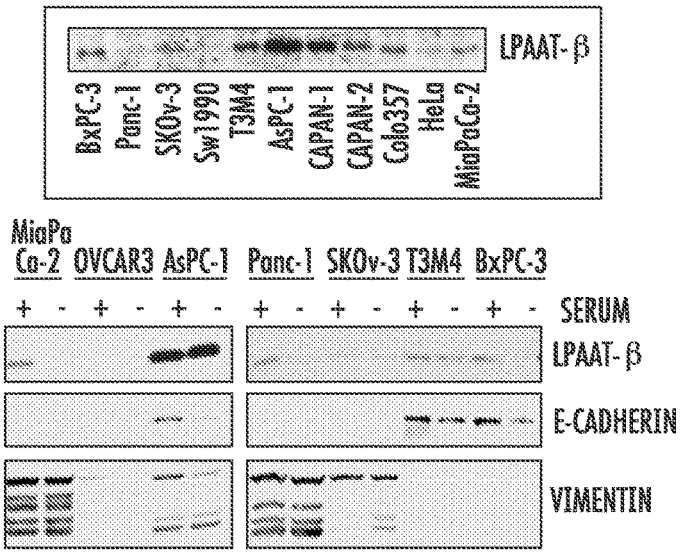
FIG. 8 shows that LPAAT-beta expression in pancreatic cancer cells increases with serum stimulation as assessed by Western blot.
Figure 9A:
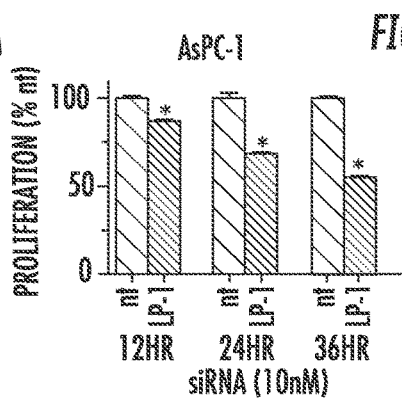
FIGS. 9A-9D show siRNA knockdown of LPAAT-beta inhibits proliferation of pancreatic cancer cell lines.
Figure 9B:
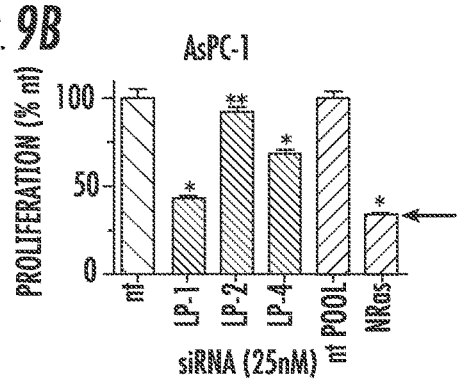
Figure 9C:
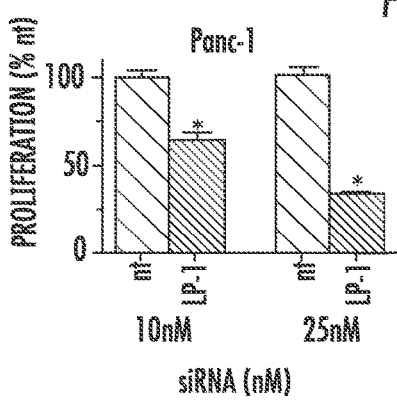
Figure 9D:
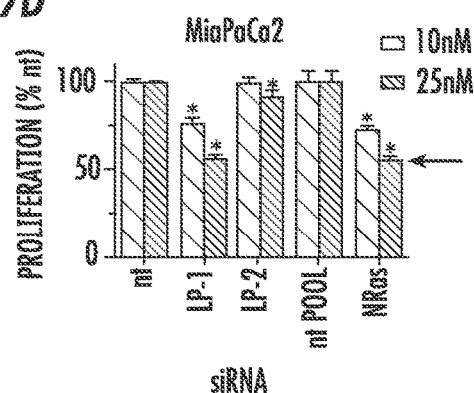
Figure 11:
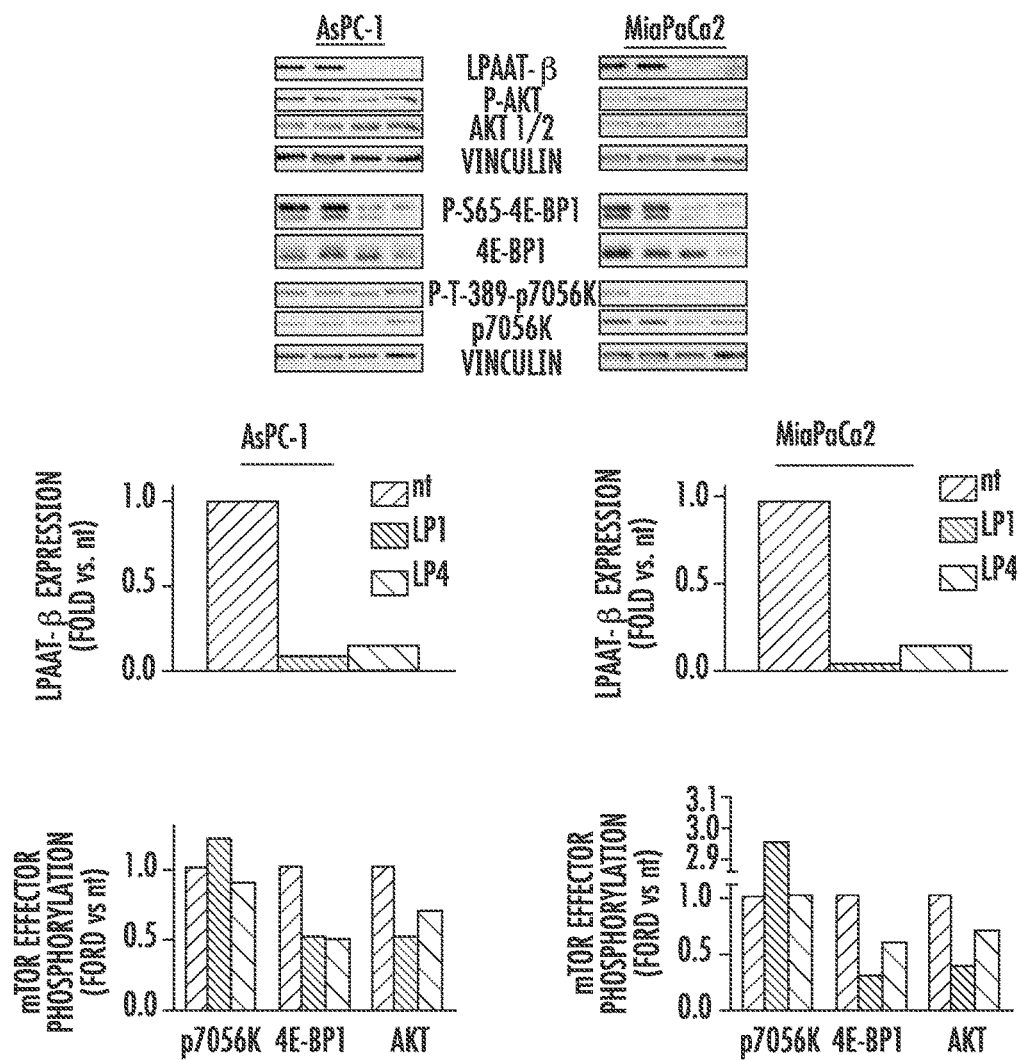
FIG. 11 shows SiRNA knockdown of LPAAT-beta mTOR signaling as shown by decreased p-S65-4EBP1, p-T389-p70S6K and pOAkt.
Figure 12A:
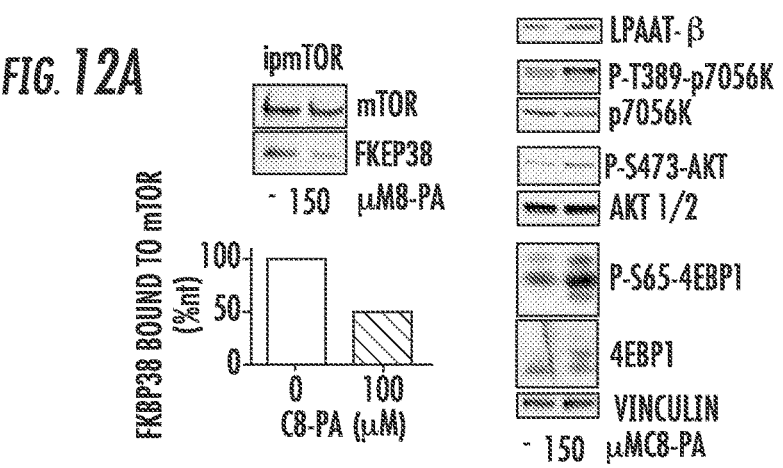
FIGS. 12A-12B show that stimulation with PA decreases association of mTOR with FKBP38 (A). This is associated with increased mTOR activation and increased p-p70S6K, p-Akt and p-4EBP1. SiRNA inhibition of LPAAT-beta decreases PA levels resulting in increased association of mTOR with FKBP38 (B).
Figure 12B:
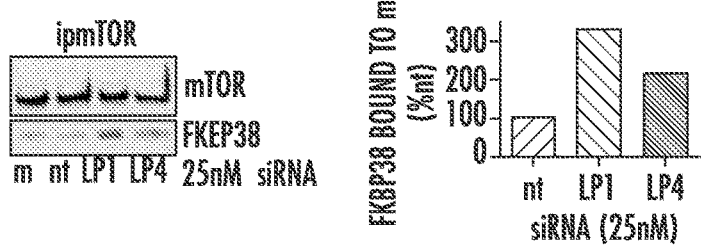
Figure 13:
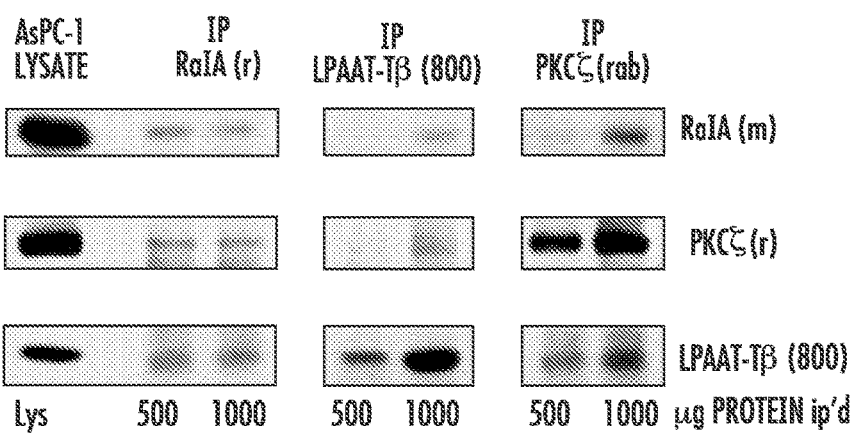
FIG. 13 shows that LPAAT-b, Ral-A and PKC-z associate with each other. By use of triple reciprocal co-immunoprecipitation, it is shown that i) RalA co-immunoprecipitates with LPAAT-beta; ii) PKC-zeta co-immunoprecipitates with LPAAT-beta; iii) RalA co-immunoprecipitates with PKC-zeta. This suggests that these 3 proteins are in a complex with each other in the cell. Using a proteomic approach the interaction of RalA with LPAAT-beta was confirmed. Proteins co-immunoprecipitated with LPAAT-beta were run on SDS-PAGE. The bands recovered and sent to the proteomics core for peptide mapping and identification. RalA is the top scoring hit in the 25 kDa range.
Figure 16:
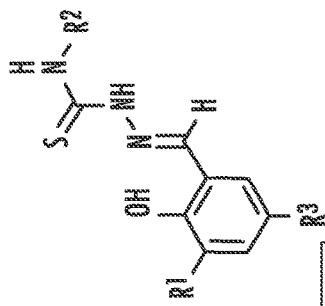
FIG. 16 shows data from a selective SAR with HM6-009-1. It was determined that the R1 position is important. Allyl group was most active. Modifications at R2 was not well tolerated. Halogen groups at R3 showed increased activity.
Figure 17:
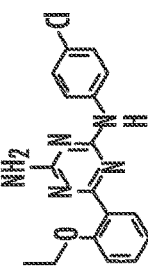
FIG. 17 shows efficacy for certain compounds. HM6-164-1 showed good activity in 3 different pancreatic cancer cell lines. Activity was submicromolar in the screening assay a low micromolar in the thin layer chromatography assay.
Figure 18:
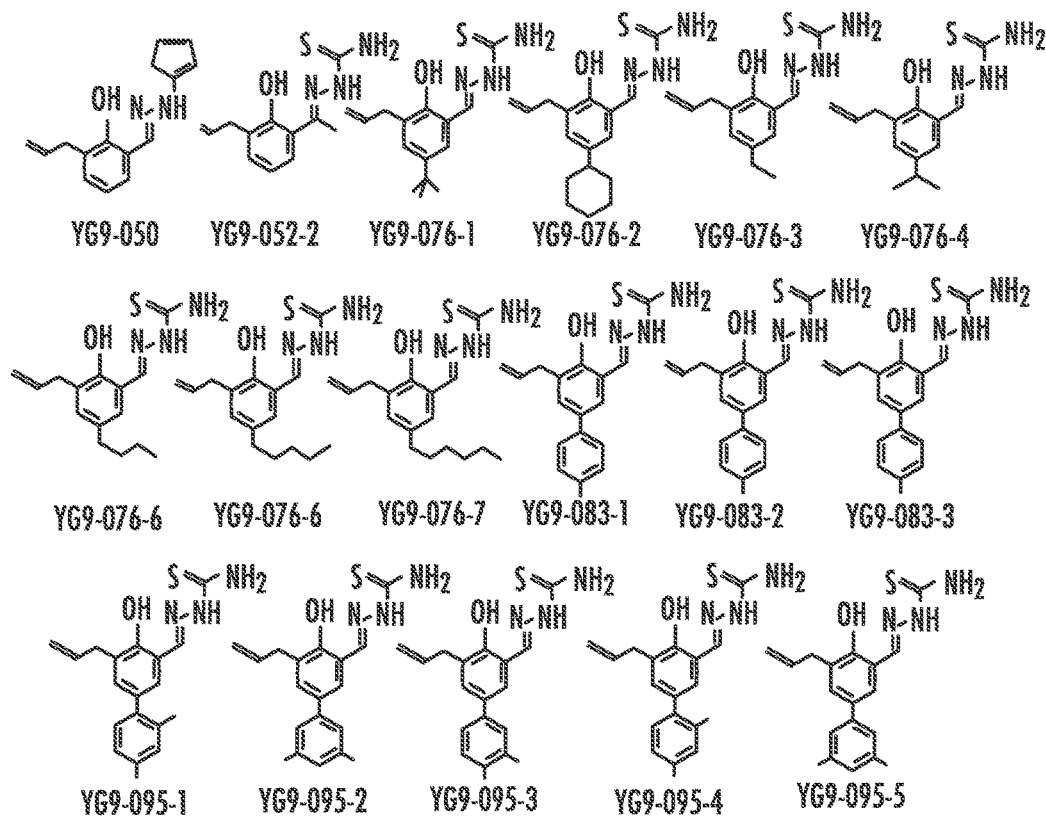
FIG. 18 shows compounds according to the disclosed subject matter.
Figure 19:
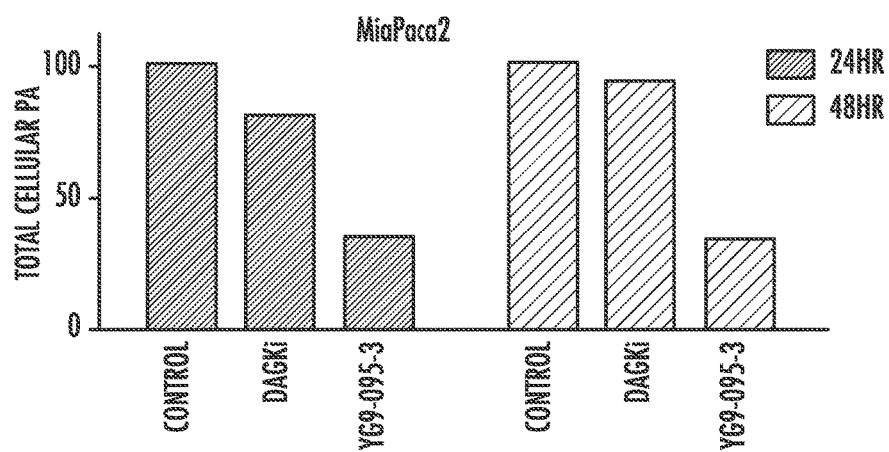
FIG. 19 shows YG9-095-3 reduces total cellular PA levels as measured by mass spectroscopy. Inhibition is by more than 50% Inhibition is greater than that seen with a known DAGK inhibitor. DAGK is an enzyme that can also increase PA levels. Since the treatment was done on intact cells, this also shows that YG9-095-3 is cell membrane permeable.
Figure 20:
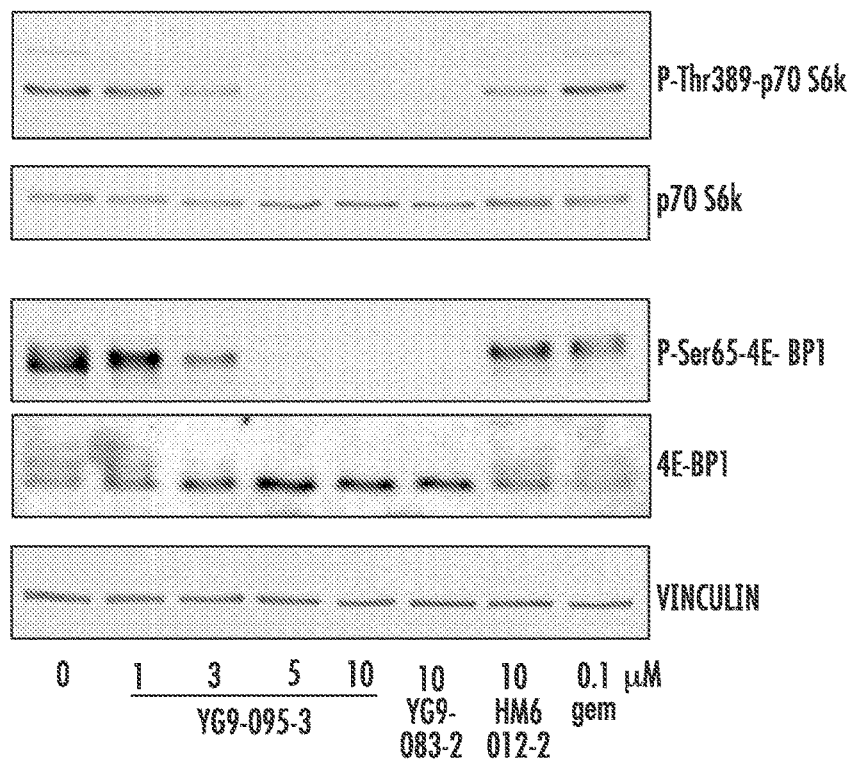
FIG. 20 shows LPAAT-beta inhibitor YG9-095-3 inhibits mTOR signaling in a manner similar to siRNA to LPAAT-beta. P-p70S6k and p-4EBP1 are decreased by treatment at 3 micromolar or higher.
Figure 21:
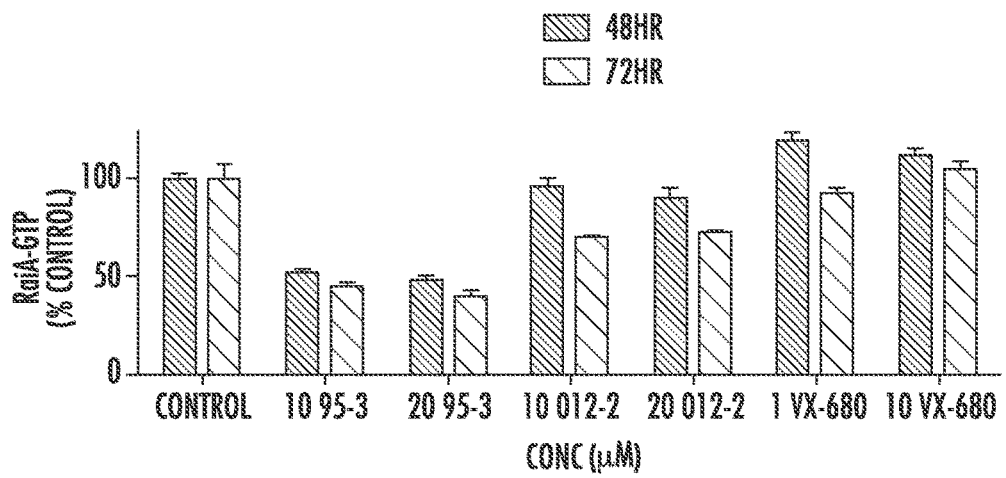
FIG. 21 shows LPAAT-beta inhibitor YG9-095-3 inhibits RalA activation by 50%. Aurora kinase inhibitors fail to do this consistently. Structurally similar compounds that are inactive in the LPAAT-beta inhibition assay (HM6-012-2) also fail to do this. Therefore this inhibitor can target the RalA effector arm as well as mTOR which few compounds can do.
Figure 22:
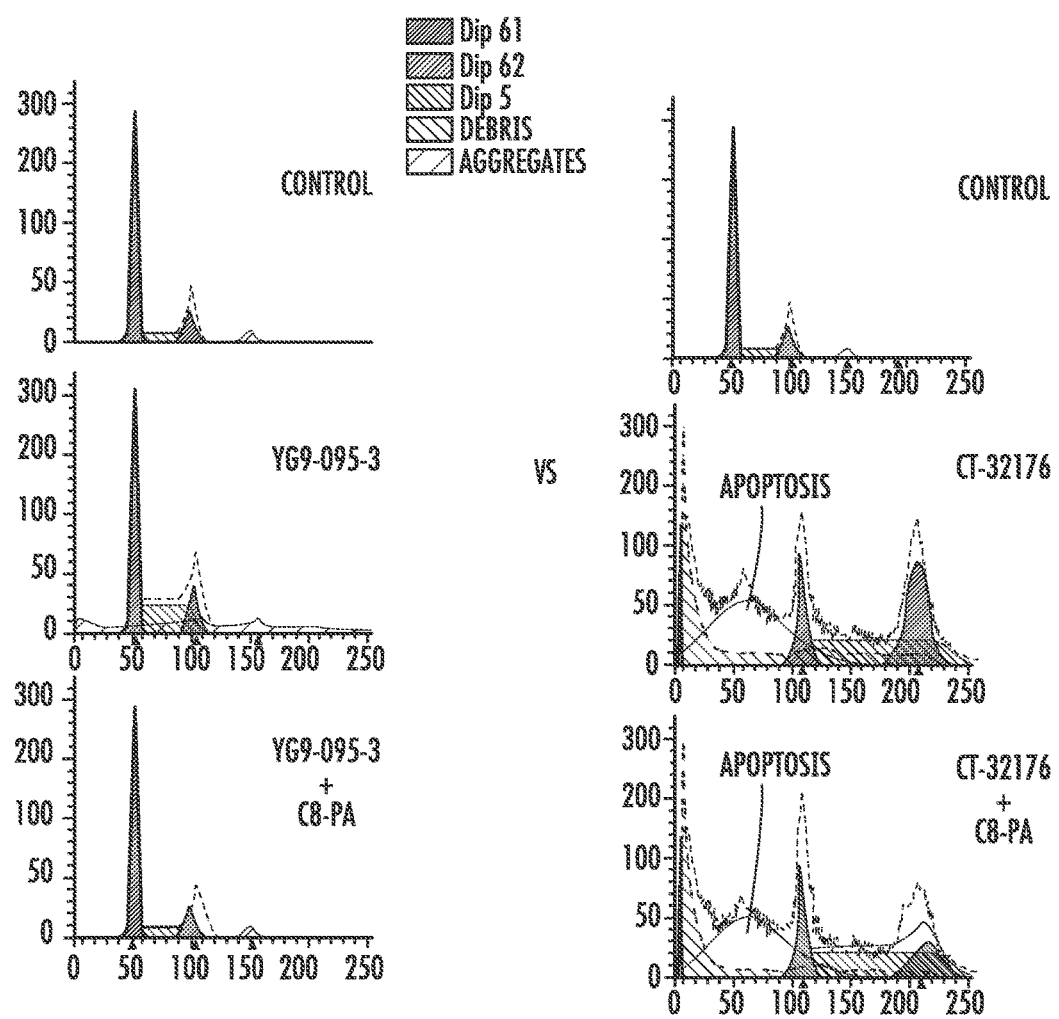
FIG. 22 shows LPAAT-beta inhibitor YG9-095-3 inhibits cell cycle progression in pancreatic cancer cells with an S-phase arrest and accumulation. Cells can be rescued from this effect by supplying exogenous PA which suggest that the effect is PA dependent. The first generation LPAAT-beta inhibitors as exemplified by CT-32176 produce a different pattern of cell cycle disruption. Cells are not rescued from this disruption by exogenous PA suggesting that the cell cycle and growth inhibitory effects of that compound are from off target effects.
Figure 23:
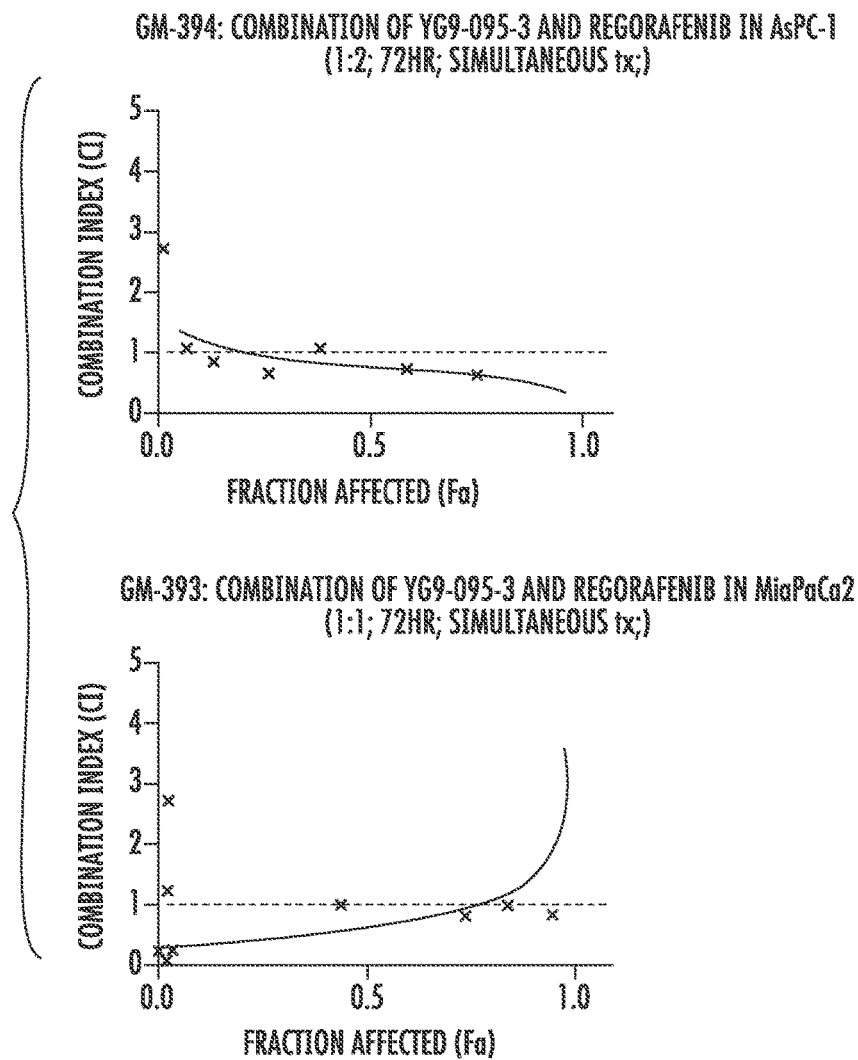
FIG. 23 shows that combination treatment of pancreatic cancer cells with LPAAT-beta inhibitor YG9-095-3 and raf/VEGF inhibitory regorafenib shows additive to synergistic inhibition. This is important for the use of YG9-095-3 in combination with standard therapy for Kras mutant colon cancer.
Figure 24:
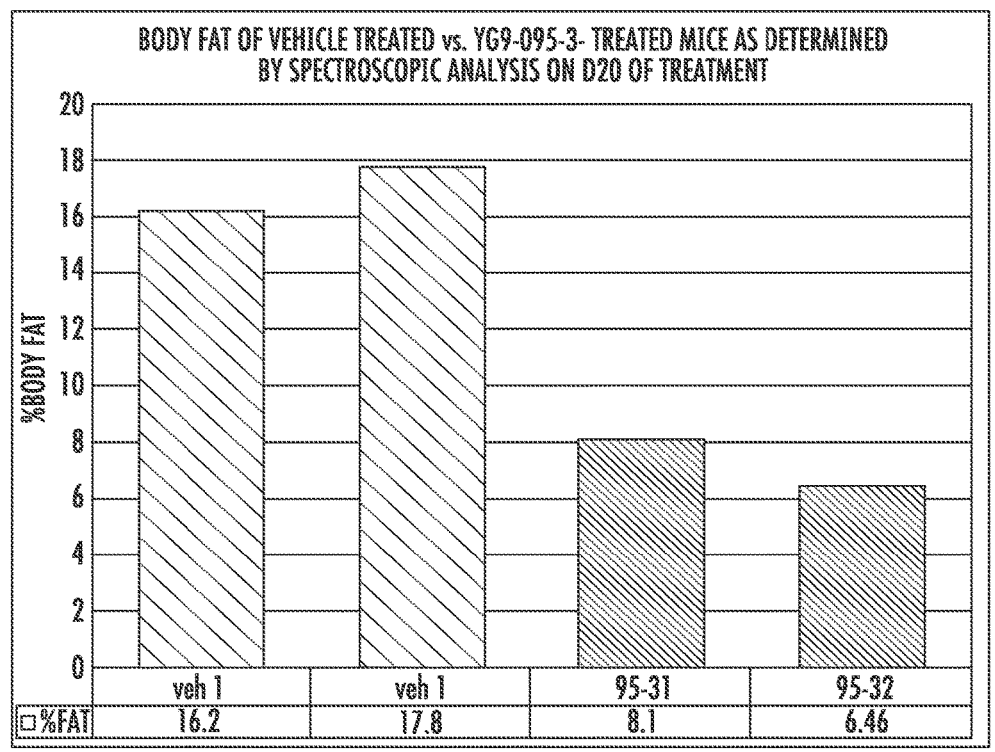
FIG. 24 is a graph that shows that as a compound that targets LPAAT-beta, YG9-095-3 treated mice have a decrease in body fat percentage by 50% after 20 days of treatment compared to vehicle treated controls as measured by MRI. YG9-095-3 can be a useful compound for the treatment of obesity as well as cancer.

The ability of selected compounds from the libraries 6, 15 and 19 to inhibit the growth of MiaPaCa2 human pancreatic cancer cells was investigated. Human pancreatic carcinoma (MiaPaCa2) cells were plated at a low confluency into 96-well tissue culture-treated plates. After allowing cells to attach and grow overnight at 37 degrees in a 5% $CO_2$ incubator, growth medium was replaced with fresh medium (100 μl/well) containing compounds in a range from 0.1-100 μM. All treatments were made from 500× stock solutions in DMSO, and the control wells received an equivalent amount of DMSO in medium. After 72 hours of growth in the presence of the compounds, Alamar blue was added to the wells according to the manufacturer's instructions (Life Technologies, Grand Island, N.Y.) and cells were incubated in its presence for 2-3 hours. Fluorescence readings were performed using a Biotek Synergy II plate reader with emission/excitation wavelengths of 530/590 nm Inhibition of proliferation compared to vehicle control was calculated, and the $IC_{50}$ for inhibition of proliferation over 72 h was determined using a non-linear, least squares (ordinary) curve fit in GraphPad Prism 6.0, as shown in Table 5. Calculated $IC_{50}$s are representative of at least three independent experiments. FIG. 2 shows the 10-fold progression of inhibition of proliferation by the compounds from the lead 6a to the most active of the compounds in Table 5 (19t).

TABLE 5

Inhibition of Pancreatic Cancer cell growth by selected thiosemicarbazones 6, 15 and 19.

| | $IC_{50}$ (μM) (DTNB assay) | $IC_{50}$ (μM) (TLC assay) | $IC_{50}$ (μM) MiaPaCa2 |
|---|---|---|---|
| 6a | 0.86 ± 0.52 | 33 ± 13 | 38 ± 17 |
| 6j | 0.85 ± 0.56 | 48 ± 15 | 36 ± 20 |
| 15a | 0.65 ± 0.42 | 35 ± 18 | 23 ± 15 |
| 19a | 0.17 ± 0.09 | 3.3 ± 1.2 | 14 ± 5.5 |
| 19h | 0.16 ± 0.07 | 1.4 ± 1.1 | 12 ± 3.3 |
| 19o | 0.18 ± 0.07 | 4.2 ± 1.2 | 5.8 ± 1.6 |
| 19p | 0.32 ± 0.07 | 2.5 ± 1.4 | 7.4 ± 2.3 |
| 19r | 0.52 ± 0.23 | 2.1 ± 0.9 | 7.6 ± 0.9 |
| 19s | 0.36 ± 0.10 | 2.4 ± 0.7 | 6.3 ± 2.9 |
| 19t | 0.57 ± 0.27 | 17 ± 7.3 | 4.9 ± 2.0 |
| 19v | 0.28 ± 0.02 | >10 | 7.8 ± 2.7 |
| 19w | 0.67 ± 0.16 | 9.2 ± 4.2 | 7.2 ± 3.1 |

Additional Screens

A total of 10380 compounds at 100 μM and another 824 compounds at 10 μM were screened against LPAAT. From this initial screen 7 compounds were isolated.

| | | >25% | >50% | hit rate overall | hit rate >50% |
|---|---|---|---|---|---|
| Compounds screened at 100 μM | | | | | |
| Nat Prod I & II | 102 | 6 | 2 | 7.8 | 2.0 |
| Enzo Kinase Inhibitors Set | 80 | | | | |
| Enzo Nuc Receptor Ligand Set | 76 | 8 | 4 | 7.7 | 2.6 |
| NCI Chronology Set | 97 | 1 | 0 | 1.0 | 0.0 |
| NCI Clinical Collection I | 448 | 25 | 4 | 6.5 | 0.9 |
| NCI Clinical Collection II | 281 | 0 | 1 | 3.2 | 0.4 |
| NCI Diversity Set 2 | 1376 | 50 | 14 | 4.7 | 1.0 |
| LOPAC | 1280 | 22 | 7 | 2.3 | 0.5 |
| LifeChem | 6640 | 295 | 95 | 5.9 | 1.4 |
| Compounds screened at 10 μM | | | | | |
| NCI Mechanistic Set (10 μM) | 824 | 54 | 8 | 7.5 | 1.0 |

A hit from the library showed good inhibition in both the spectrophotometric screening assay (indirect) and Thin Layer chromatography assay (direct measure of LPAAT-beta inhibition). This was designated HM6-009-1.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound having Formula I,

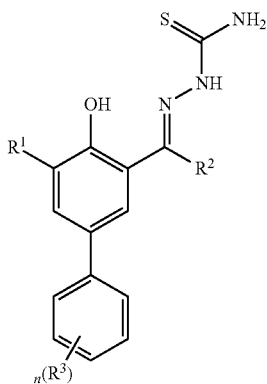

I wherein,
$R^1$ is F, Cl, Br, $CF_3$, or $C_{1-5}$ alkyl, or $C_{2-5}$ alkenyl,
$R^2$ is H or optionally substituted $C_{1-6}$ alkyl or phenyl; and
n is 1, 2, 3, 4 or 5; and each $R^3$ is, independent of any other, F, Cl, Br, OH, CN, $NH_2$, optionally substituted $C_{1-8}$ alkyl, $C_{1-8}$ alkenyl, $OC_1$-$C_8$ alkyl, $OC_{2-8}$ alkenyl, $NHC_1$-$C_8$ alkyl, $NHC_2$-$C_8$ alkenyl, $C_{5-6}$ cycloalkyl, phenyl, $COC_{1-8}$ alkyl, $COC_{5-6}$ cycloalkyl, or CO phenyl; $CONHC_{1-8}$ alkyl, $CONHC_{5-6}$ cycloalkyl, or CONHphenyl; or $R^2$ and $R^3$ can form a fused aryl or heteroaryl;

wherein optional substituents are selected from F, Cl, Br, OH, CN, $C_{1-8}$ alkyl, $OC_{1-8}$ alkyl, phenyl, CN, $C_{1-4}$ haloalkyl, or a pharmaceutical acceptable salt thereof.

2. The compound of claim 1, wherein $R^1$ is a $C_{2-4}$ alkyl.
3. The compound of claim 1, wherein $R^1$ is propenyl.
4. The compound of claim 1, wherein $R^2$ is H.
5. The compound of claim 1, wherein $R^2$ is methyl.
6. The compound of claim 1, wherein n is 2.
7. The compound of claim 1, wherein n is 3.
8. The compound of claim 1, wherein n is 2 and each $R^3$ is chosen from F, Cl, Br, and CN.
9. The compound of claim 1, wherein the compound inhibits LPAAT-β.
10. A method of treating cancer in a subject, comprising: administering a therapeutically effective amount of a compound of claim 1 to a subject in need thereof.
11. The method of claim 10, wherein the cancer is pancreatic cancer.
12. The method of claim 10, wherein the compound is administered with an anti-cancer agent.
13. The method of claim 10, wherein the cancer is colon cancer.
14. The method of claim 10, wherein the subject is also administered regorafenib.
15. A method of treating obesity in a subject, comprising: administering a therapeutically effective amount of a compound of claim 1 to a subject in need thereof.

* * * * *